(12) United States Patent
Arnissolle

(10) Patent No.: US 7,762,983 B2
(45) Date of Patent: Jul. 27, 2010

(54) MEDICAL DEVICE FOR DISTRIBUTING AT LEAST ONE FLUID

(75) Inventor: Yves Arnissolle, Saint Genis-Laval (FR)

(73) Assignee: SEDAT, Irigny (FR)

( * ) Notice: Subject to any disclaimer, the term of this patent is extended or adjusted under 35 U.S.C. 154(b) by 1264 days.

(21) Appl. No.: 10/868,340

(22) Filed: Jun. 16, 2004

(65) Prior Publication Data

US 2005/0015012 A1  Jan. 20, 2005

(30) Foreign Application Priority Data

Jun. 17, 2003 (FR) .................................. 03 07284

(51) Int. Cl.
*A61M 29/00* (2006.01)
*A61M 31/00* (2006.01)
*A61M 37/00* (2006.01)

(52) U.S. Cl. .................. 604/99.02; 604/67; 604/82; 604/97.02; 604/99.04

(58) Field of Classification Search ............ 604/67, 604/89, 96.01, 97.02, 97.03, 173, 470, 99.01–99.04
See application file for complete search history.

(56) References Cited

U.S. PATENT DOCUMENTS

| | | | | |
|---|---|---|---|---|
| 4,740,203 A | * | 4/1988 | Hoskins et al. | 604/191 |
| 4,793,351 A | * | 12/1988 | Landman et al. | 606/195 |
| 4,935,009 A | * | 6/1990 | Caldwell et al. | 604/507 |
| 5,515,851 A | | 5/1996 | Goldstein | |
| 5,545,140 A | * | 8/1996 | Conero et al. | 604/154 |
| 6,063,052 A | | 5/2000 | Havrilla et al. | |
| 6,197,000 B1 | | 3/2001 | Reilly et al. | |
| 6,471,671 B1 | * | 10/2002 | Urick et al. | 604/98.01 |
| 6,471,674 B1 | * | 10/2002 | Emig et al. | 604/131 |
| 2003/0032862 A1 | * | 2/2003 | Ota et al. | 600/158 |

FOREIGN PATENT DOCUMENTS

| | | |
|---|---|---|
| DE | 44 26 387 A | 8/1995 |
| EP | 619 122 A | 10/1994 |
| WO | WO 94/13204 A | 6/1994 |

\* cited by examiner

*Primary Examiner*—Nicholas D Lucchesi
*Assistant Examiner*—Victoria P Campbell
(74) *Attorney, Agent, or Firm*—Sughrue Mion, PLLC

(57) ABSTRACT

The medical device for distributing fluid comprises:
 a syringe (12) for distributing a contrast product;
 an actuator (28) which is suitable for acting on the syringe in order to ensure that the contrast product flows at a pressure greater than 30 bar;
 an injection outlet (14) for injecting the contrast product towards the body of a patient, and being connected to the syringe (12);
 it further comprises:
 an inflation outlet (16) for a balloon;
 a distributor (32) which is connected at the outlet of the syringe (12) and which is suitable for selectively connecting the same syringe (12) to the injection outlet (14) or to the inflation outlet (16); and
 means (20; 22) for controlling the distributor (32) between a first state which connects the syringe to the injection outlet (14) and a second state which connects the syringe (12) to the inflation outlet (16).

14 Claims, 5 Drawing Sheets

MEDICAL DEVICE FOR DISTRIBUTING AT LEAST ONE FLUID

TECHNICAL FIELD

The present invention relates to a medical device for distributing at least one fluid, of the type comprising:
- a syringe for distributing a contrast product;
- an actuator which is suitable for acting on the syringe in order to ensure that the contrast product flows at a pressure greater than 30 bar;
- an outlet for injecting the contrast product towards the body of a patient, which outlet is connected to the syringe.

BACKGROUND TO THE INVENTION

Currently, it is known to carry out surgical interventions on the blood circulation system of a human being by the endoluminal route.

These methods of treatment and intervention require angiography and angioplasty procedures.

In order to follow the different phases of intervention, it is known for the practitioner to view the treated regions on a medical observation device which displays the treated region on a screen.

In order to allow the blood circulation system to be seen in a satisfactory manner, and in particular the region which is to be treated, it is necessary to inject, during some phases of the intervention and at specific locations, a contrast product which appears in an identifiable manner on the screen.

To this end, the practitioner uses several types of device, depending on the type of operation which has to be carried out or in accordance with the phases of this operation.

In order to inject large volumes of contrast product, in the order of 200 ml, this volume being injected rapidly via a catheter having a small cross-section, the practitioner uses a so-called "high-pressure" injector. An injector of this type is capable of causing the volume of the contrast product to circulate at high speed via the catheter, this high speed being achieved by a high pressure, in the order of 1200 psi (85 bar), in the catheter.

Furthermore, the practitioner is obliged to use a coronary arteriography set which allows smaller quantities of the contrast product to be injected manually by means of a syringe and measurements of artery or vein pressure to be taken. This set generally also allows a cleaning solution to be injected, such as a solution of sodium chloride.

Finally, in order to dilate some arteries or veins whose cross-section can be obstructed by abnormal deposits, the practitioner is obliged to arrange an inflatable balloon in the artery or vein which is to be treated and to connect this balloon to an inflation device which allows the balloon to be pressurised and the artery or vein to be dilated. These inflation devices are suitable for injecting a contrast product at a high pressure, in the order of 30 bar, in order to allow the dilation of the balloon, whilst ensuring that the balloon can be viewed in a satisfactory manner on a screen.

Each of these devices which allows the contrast product to be injected at different pressures is associated with follow-up devices which allow the injection pressure of the contrast product to be measured as well as the duration and number of these injections.

It will be appreciated that the interventions which require angiography and angioplasty procedures use a number of medical devices, thereby complicating the task of the practitioner and making these interventions costly to carry out.

SUMMARY OF THE INVENTION

The object of the invention is to provide a medical device for distributing fluid, which device allows the task of the practitioner to be facilitated during these angiography and angioplasty procedures and which reduces the cost of these interventions.

To this end, the subject-matter of the invention is a medical device of the above-mentioned type, characterised in that it further comprises:
- an inflation outlet for a balloon;
- a distributor which is connected at the outlet of the syringe and which is suitable for selectively connecting the same syringe to the injection outlet or to the inflation outlet; and
- means for controlling the distributor between a first state which connects the syringe to the injection outlet and a second state which connects the syringe to the inflation outlet.

According to specific embodiments, the device comprises one or more of the following features:
- it comprises a storage reservoir for the contrast product, which reservoir is connected to the distributor and the distributor has a third state which connects the reservoir to the syringe;
- it further comprises a storage reservoir for an auxiliary fluid and means for circulating the auxiliary fluid;
- it comprises a switching valve which is interposed between the distributor and the injection outlet, which switching valve is connected to the means for circulating the auxiliary fluid, and the switching valve can be switched between a first state in which the means for circulating the auxiliary fluid are connected to the injection outlet and a second state in which the means for circulating the auxiliary fluid are connected to the distributor;
- the switching valve comprises a moveable sliding valve which is held in a rest position, which defines the first state of the switching valve, under the action of a spring when there is no pressurised contrast product coming from the distributor, and the sliding valve is moveable, under the action of the pressurised contrast product coming from the distributor, towards a position of passage which defines the second state of the switching valve;
- it comprises a pressure sensor which is connected to the injection outlet via the switching valve;
- the pressure sensor is connected to the switching valve in such a manner that the pressure sensor is connected to the injection outlet when the switching valve is in the first state thereof;
- it comprises a mixer which is interposed between the distributor and the inflation outlet and the mixer is further connected to the means for circulating the auxiliary fluid in order to ensure that the contrast product and the auxiliary fluid are mixed;
- it comprises a selector which is connected at the outlet of the means for circulating the auxiliary fluid and at the inlet of the mixer and the switching valve, and the selector can be switched between a first state in which the means for circulating the auxiliary fluid are connected to the switching valve and a second state in which the means for circulating the auxiliary fluid are connected to the mixer; and
- it comprises means for following up and adjusting the pressure of the contrast product at the syringe outlet.

BRIEF DESCRIPTION OF DRAWINGS

The invention will be better understood from a reading of the following description, given purely by way of example and with reference to the drawings, in which.

DESCRIPTION OF PREFERRED EMBODIMENT

Figure 1:
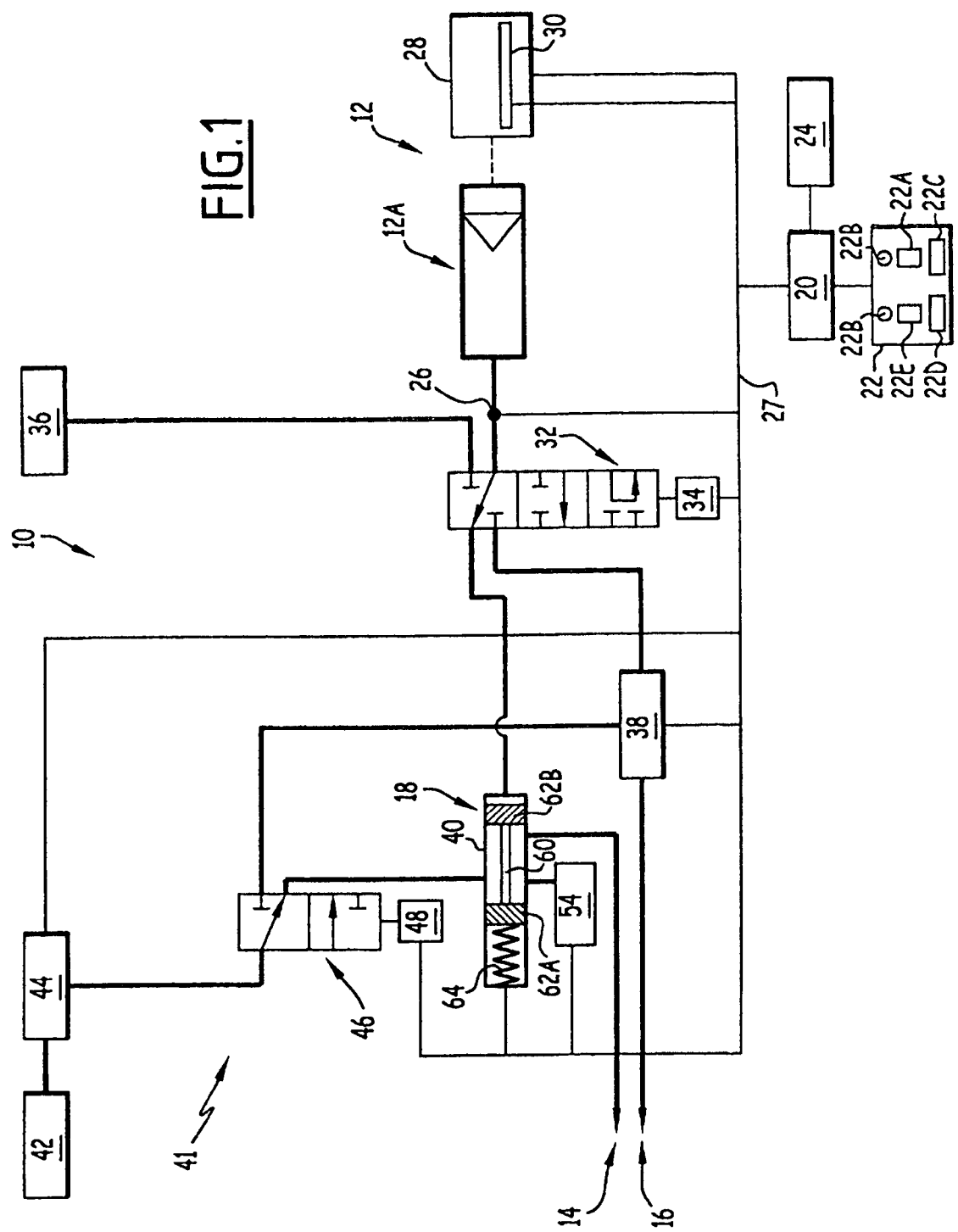
FIG. 1 is a schematic view of the medical device for distributing fluid according to the invention, illustrated in the rest position.

The device 10 for distributing medical fluids illustrated in FIG. 1 substantially comprises means 12 for pressurizing a contrast product and for distributing the product towards one or other of two separate outlets 14 and 16.

The injection outlet 14 is constituted by a connector which allows a distribution catheter for the contrast product to be connected at a specific point of the body. This catheter is advantageously equipped with a Y connector which allows a filamentary surgical tool to be introduced during angioplasty.

The outlet 14 is more precisely capable of distributing the contrast product, or a rinsing solution, and of allowing the device to be connected to the body in order to carry out a measurement of internal pressure.

The inflation outlet 16 of the balloon is constituted by a connector which allows a flexible connection tube to be connected to an inflatable angioplasty balloon.

The outlet is suitable for allowing the distribution of pure contrast product or a mixture of contrast product and a neutral diluting solution, such as a solution of sodium chloride.

The means for pressurising the contrast product 12 are connected to the outlets 14 and 16 by switching means 18 which will be described in detail below and which ensure a selective connection of one or other of the outlets to the means 12.

Furthermore, the device comprises an information processing unit 20 which allows the control of various elements which will be described below and the collection of information. This information processing unit 20 is connected to a remote control 22 and to a unit 24 for storing and presenting the information recorded.

The means for pressurising the contrast product 12 comprise a syringe 12A.

The syringe 12A is preferably disposable. It comprises, as known per se, a cylindrical body in which a moveable plunger is arranged. The syringe has a large capacity of between 100 and 500 ml.

The syringe 12A is received in a support (not shown) which allows the fluid and mechanical connection thereof to the other elements of the device.

This support comprises in particular a pressure sensor 26 which allows the pressure of the contrast product to be determined at the outlet of the syringe. The sensor 26 is connected to the information processing unit 20.

The various sensors, such as the sensor 26, are connected to the unit 20 via an information transmission bus 27.

In order to displace the plunger of the syringe 12A, the device is equipped with an actuator 28 which is controlled by the information processing unit 20. This actuator comprises a sensor 30 which allows the position of the syringe plunger to be determined and therefore the quantity of contrast product contained in the syringe at a given time. This sensor 30 is connected to the information processing unit 20.

The outlet of the syringe 12A is connected to a first inlet of a distributor 32 having four paths and three states. A second inlet of the distributor 32 is connected to a reservoir 36 for the contrast product.

The moveable part of the distributor 32 is connected mechanically to an actuator 34 which allows the distributor to be switched between these three positions. This actuator 34 is connected, for the control thereof, to the information unit 20.

A first outlet of the distributor 32 is connected to a first inlet of an adjustable mixer 38 which allows the contrast product to be distributed towards the inflation outlet 16.

A second outlet of the distributor 32 is connected to an inlet of a switching valve 40 which allows the distribution of contrast product towards the injection outlet 14.

The distributor 32 is suitable, in a first state, for ensuring that the outlet of the syringe 12A is connected to the second distributor outlet which is connected to the switching valve 40. The outlet of the reservoir 36 for contrast product and the first inlet of the mixer 38 are therefore isolated.

In the second state thereof, the distributor 32 ensures that the outlet of the syringe 12A is connected to the first inlet of the mixer 38, the outlet of the reservoir 36 for contrast product and the inlet of the switching valve 40 being isolated.

In the third state thereof, the distributor ensures that the reservoir 36 for contrast product is connected to the outlet of the syringe 12A, the inlets of the mixer and the switching valve being isolated.

Furthermore, the device according to the invention advantageously comprises means 41 for distributing a cleaning or diluting liquid. In the embodiment envisaged, this product is constituted by a solution of sodium chloride.

These means 41 comprise a reservoir 42 for cleaning or diluting solution. A pump 44 is provided at the outlet of this reservoir 42 in order to ensure that the fluid is circulated in the device. The pump 44 is connected, for the control thereof, to the information processing unit 20.

The outlet of the pump 44 is connected to an inlet of a selector 46 which is constituted by a distributor having three paths and two states. The moveable part of the selector is connected mechanically to an actuator 48 for the displacement thereof. This actuator 48 is controlled by the information processing unit 20.

A first outlet of the selector 46 is connected to the second inlet of the mixer 38.

The second outlet of the selector 46 is connected to a second inlet of the switching valve 40.

The selector 46 is suitable for ensuring, in a first state, that the outlet of the pump 44 and the second inlet of the switching valve are connected, the second inlet of the mixer 38 not being supplied, and, in a second state, that the pump 44 and the mixer 38 are connected, the second inlet of the switching valve 40 being isolated.

The mixer 38 can be adjusted in order to define the content of contrast product and diluting fluid in the mixture. In order to be adjusted, the mixer is connected to the information processing unit 20.

The switching valve 40 comprises an inlet for the contrast product, which inlet is connected to the second outlet of the distributor 32, and an inlet for the cleaning fluid, which inlet is connected to the second outlet of the selector 46.

Furthermore, the switching valve 40 comprises an injection outlet which is directly connected to the injection outlet 14 via a tube.

Finally, the switching valve 40 comprises a pressure measuring outlet which is connected to a pressure sensor 54. This sensor is connected to the information processing unit 20.

In order to ensure a selective connection of the inlets and outlets, the switching valve 40 is equipped with a moveable sliding valve 60 which is constituted by two pistons 62A, 62B which are connected to each other and which are mounted so as to be able to slide in a cylindrical chamber.

The sliding valve 60 is held in a rest position under the action of a spring 64. In this rest position, as illustrated in FIG. 1, the injection outlet 14 is connected to the sensor 54 via the space delimited between the two pistons 62A, 62B. In this position, the piston 62B blocks the introduction inlet for the contrast product.

Figure 2:
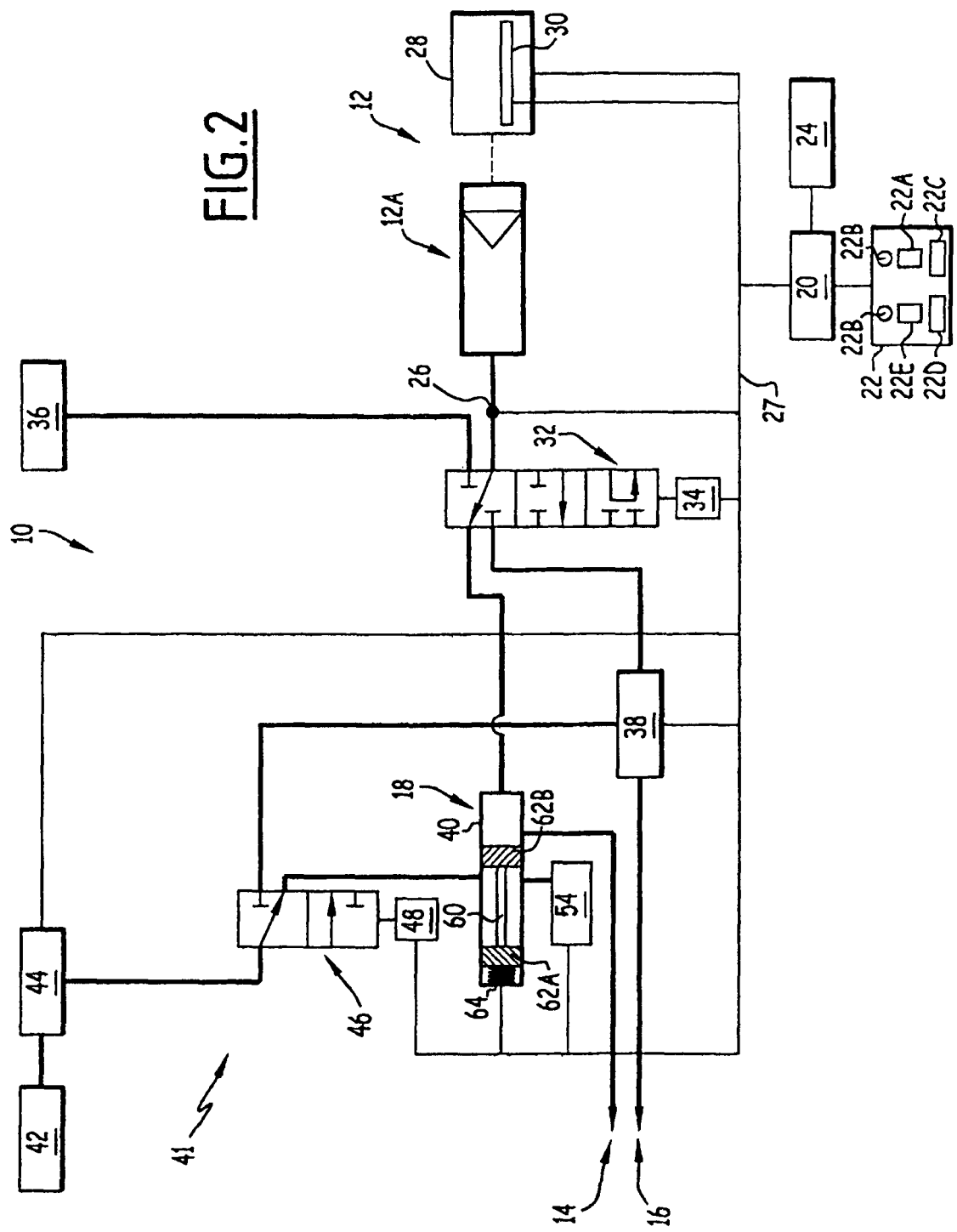
FIG. 2 is an identical view to that of FIG. 1, the device being illustrated during an injection phase of the contrast product.

Under the action of the pressure of the contrast product, the sliding valve is capable of sliding displacement, as illustrated in FIG. 2, in such a manner that the inlet for the contrast product is connected to the injection outlet for the contrast product, the sensor 54 and the inlet for the cleaning fluid being isolated from the injection outlet.

The unit 24 for storing and presenting the information comprises a display unit which allows the user to have at his disposal the pressure measured by the pressure sensor 54. It further comprises an indicator for the pressure measurement which is measured by the sensor 26 and which corresponds to the pressure present in the balloon or during injection via the path 14.

This unit is also suitable for storing the application time of these various pressures, as well as the quantity of contrast product introduced, this quantity being derived from the information provided by the position sensor 30.

The remote control 22 further comprises means 22A for adjusting the mixer 38 in order to determine the proportion of contrast product and diluting liquid.

The remote control 22 comprises means 22B for selecting the operational mode of the injecting device from an operational mode "coronary arteriography" and an operational mode "inflation".

By way of a variant, the means 22A and 22B are arranged in the information processing unit 20.

The remote control 22 further comprises means 22C for controlling the distribution of the contrast product or of a mixture of contrast products and the diluting fluid, as well as means 22D for controlling the distribution of the cleaning fluid.

Finally, the remote control 22 comprises means 22E for adjusting the operating speed of the actuator, which corresponds to the adjustment of the flow rate and the pressure which are imposed at the outlet of the syringe 12A.

The information processing unit 20 allows collection of information provided by the various sensors of the device, as well as control of the actuators which allow the state of the distributor 32 and the selector 46 to be changed and the actuator 28 and the pump 44 to be started.

It further allows the mixer 38 to be controlled in order to modify the proportion of the contrast product and the diluting liquid in the mixture obtained.

In particular, the information processing unit 20 is suitable for ensuring that the distributor and the selector are controlled in order to obtain the various operational phases, as illustrated in FIGS. 2 to 5.

When the user selects an operational mode "coronary arteriography" from the remote control 22, the information processing unit controls the distributor 32 and the selector 46 so that they are both in the first state thereof, as illustrated in FIG. 2.

In this operational mode, it is possible for the user to bring about an injection of contrast product from the injection outlet 14 by acting on the control means 22C.

During such a command, the pump 44 is maintained in the stopped state. Conversely, the actuator 28 is activated at a fixed speed in accordance with the desired flow rate at the outlet.

The contrast product contained in the syringe 12A is transferred towards the switching valve 40. The piston 62B of the sliding valve is pushed in, as illustrated in FIG. 2, in such a manner that the contrast product circulates as far as the injection outlet 14.

When the practitioner wishes to carry out a pressure measurement of the patient, he controls the stopping of the injection from the remote control. The stopping of the actuator 28 is then controlled in such a manner that, with the pressure of the contrast product being reduced, the sliding valve of the switching valve 40 returns to the position of FIG. 1. The sensor 54 is then connected to the injection outlet 14 and is suitable for providing pressure information which is representative of the pressure of the patient in the region of the connection point of the injection outlet 14.

Figure 3:
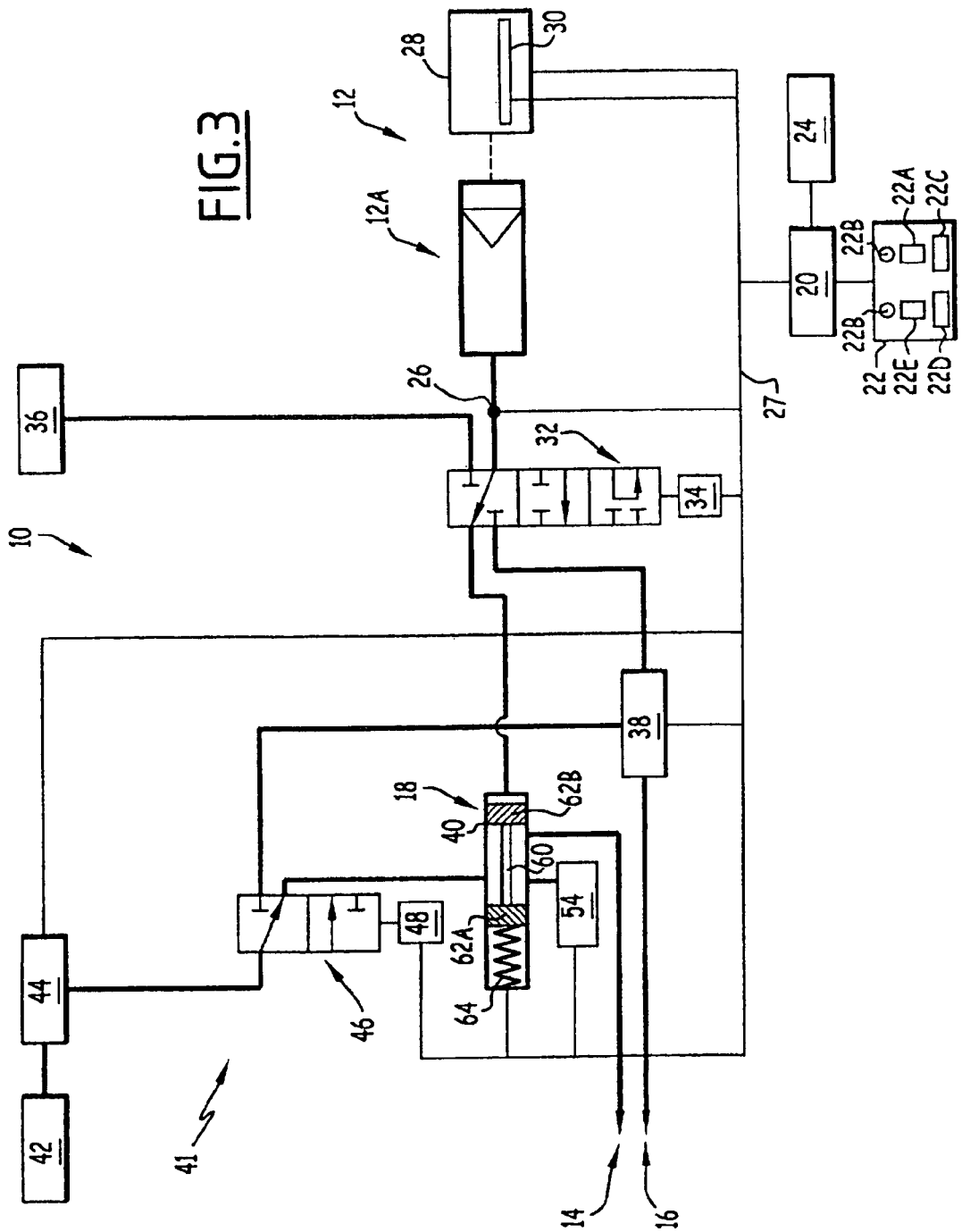
FIG. 3 is an identical view to that of FIG. 1, the device being illustrated during an injection phase of a cleaning product.

When the practitioner wishes to carry out a cleaning operation, by injecting the cleaning liquid contained in the reservoir 42, he acts on the control means 22D of the remote control. The distributor and the selector are then retained in or brought into the first state thereof, the pump 44 is activated and the actuator 28 is stopped or held in a stopped state, as illustrated in FIG. 3.

Under the action of the pressure of the cleaning fluid, the cleaning fluid circulates via the switching valve 40, more precisely in the space defined between the pistons 62A, 62B. The cleaning fluid then circulates as far as the injection outlet 14.

In order to bring about the inflation of a balloon, the user switches the device to "inflation" mode from the remote control 22.

Figure 4:
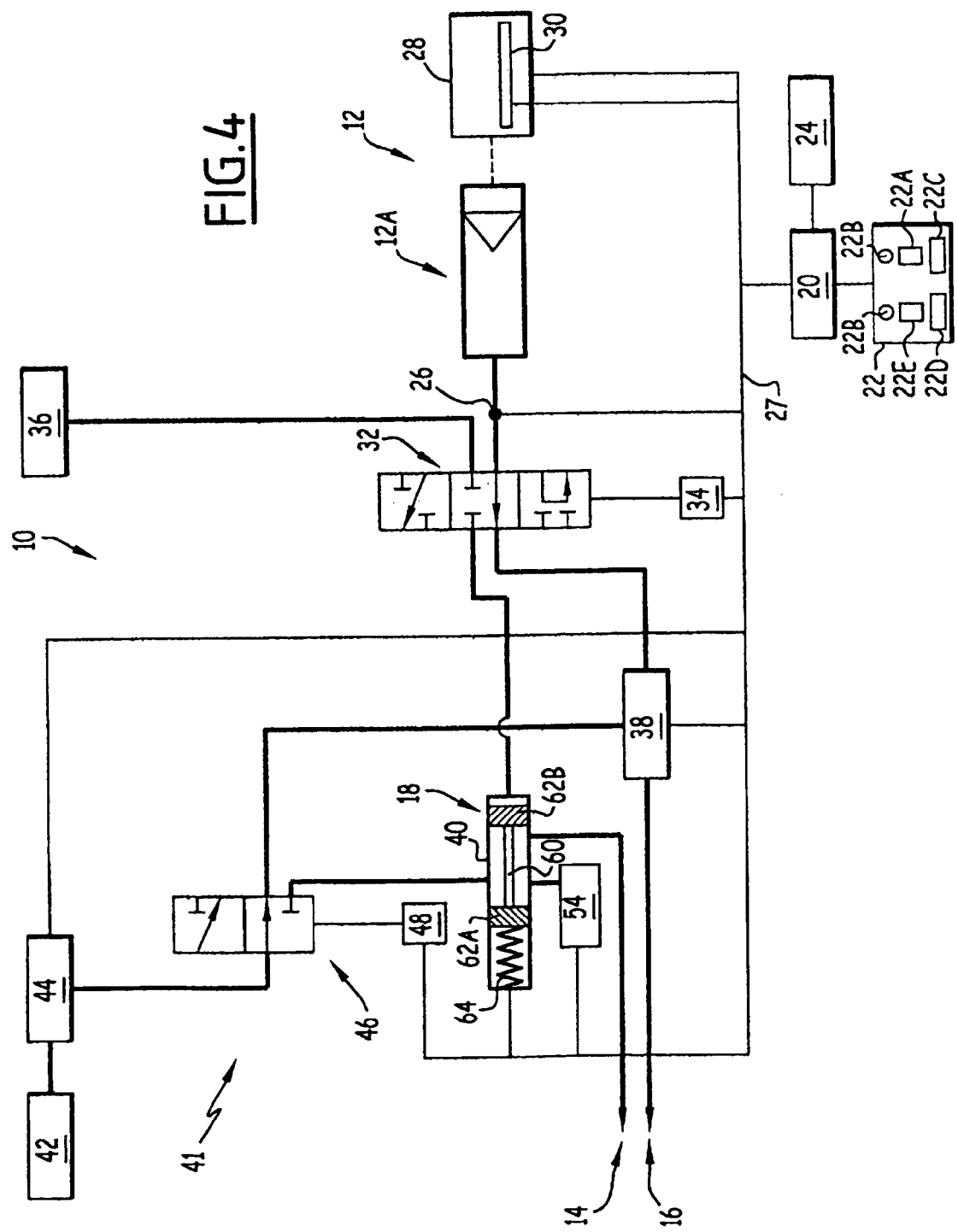
FIG. 4 is an identical view to that of FIG. 1, the device being illustrated during an inflation phase of a balloon.

The information processing unit 20 ensures that the distributor 32 and the selector 46 are automatically switched into the second state thereof, as illustrated in FIG. 4.

The pump 44 and the actuator 28 are activated.

Since the switching valve 40 is no longer being supplied either with contrast product or with cleaning liquid, it is in the rest position thereof.

As illustrated in FIG. 4, the mixer 38 is then supplied with contrast product and diluting liquid. In accordance with the proportion of the mixture adjusted from the remote control, a mixture of contrast product and diluting liquid is distributed under pressure towards the inflation outlet 16.

The pressure in the balloon is controlled from the unit 24 for storing and presenting the information recorded.

Finally, and in an automatic manner, the device ensures that the syringe 12A is filled from the contrast product contained in the reservoir 36 when the information processing unit 20 determines, based on the information obtained by the sensor 30, that the syringe 12A is insufficiently full.

Figure 5:
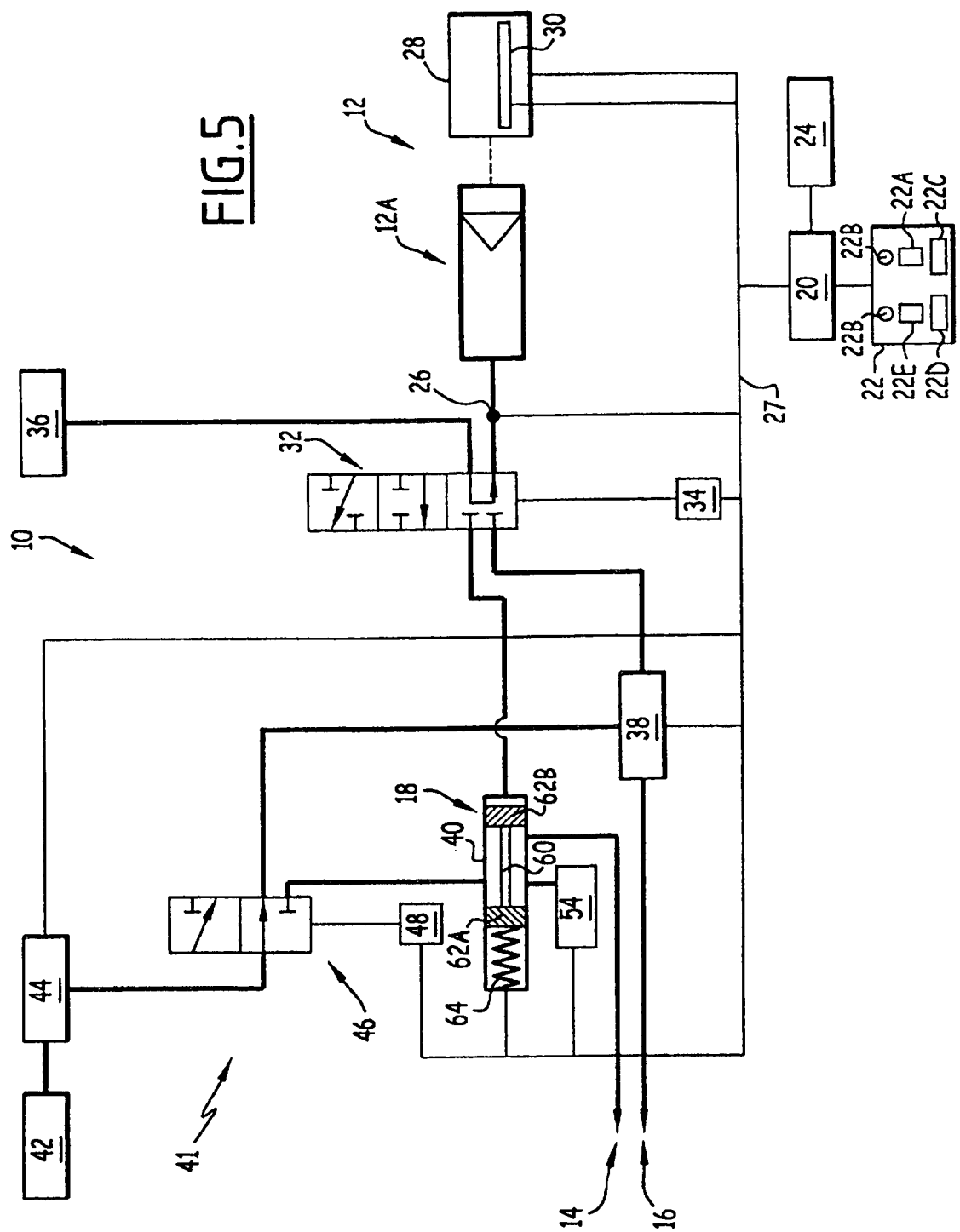
FIG. 5 is an identical view to that of FIG. 1, the device being illustrated during a filling phase of the syringe.

To this end, the distributor 32 is automatically brought into the third state thereof, as illustrated in FIG. 5, whilst the selector 46 is left in the first or second state thereof. In this state, the pump 44 is switched off and the actuator 28 is controlled in order to ensure that the plunger is displaced away from the syringe outlet so as to draw in the contrast product contained in the reservoir 36 via the device 32. After the syringe has been filled, the distributor 32 is returned to the initial state thereof.

It will be appreciated that, with a device of this type, the same source of contrast product is used simultaneously to ensure the inflation of a balloon via the inflation outlet 16 and the injection of contrast product directly into the patient via the outlet 14.

Furthermore, the various injections and inflations are controlled from the same remote control and the measurements recorded from the patient are displayed in the same unit for storing and presenting the information recorded, which facilitates the carrying out of operations by the practitioner.

The invention claimed is:

1. Medical device for distributing fluid, comprising:
a syringe for distributing a contrast product;
an actuator which is suitable for acting on the syringe in order to ensure that the contrast product flows at a pressure greater than 30 bar;
an injection outlet for injecting the contrast product towards the body of a patient, wherein the outlet is connected to the syringe;
characterised in that it further comprises:
an inflation outlet for a balloon;
a distributor which is connected at an outlet of the syringe and which is suitable for selectively connecting the same syringe to the injection outlet or to the inflation outlet;
means for controlling the distributor between a first state, which connects the syringe to the injection outlet but not to the inflation outlet, and a second state which connects the syringe to the inflation outlet, and
a storage reservoir for the contrast product, which reservoir is connected to the distributor, wherein the distributor has a third state which connects the reservoir to the syringe.

2. Device according to claim 1, wherein it further comprises a storage reservoir for an auxiliary fluid and means for circulating the auxiliary fluid.

3. Device according to claim 2, wherein it comprises a switching valve which is interposed between the distributor and the injection outlet, wherein the switching valve is connected to the means for circulating the auxiliary fluid, and wherein the switching valve can be switched between a first state in which the means for circulating the auxiliary fluid are connected to the injection outlet and a second state in which the means for circulating the auxiliary fluid are connected to the distributor.

4. Device according to claim 3, wherein the switching valve comprises a moveable sliding valve which is held in a rest position, which defines the first state of the switching valve, under the action of a spring when there is no pressurised contrast product coming from the distributor, and wherein the sliding valve is moveable, under the action of the pressurised contrast product coming from the distributor, towards a position of passage which defines the second state of the switching valve.

5. Device according to claim 3, wherein it comprises a pressure sensor which is connected to the injection outlet via the switching valve.

6. Device according to claim 5, wherein the pressure sensor is connected to the switching valve in such a manner that the pressure sensor is connected to the injection outlet when the switching valve is in the first state thereof.

7. Medical device for distributing fluid, comprising:
a syringe for distributing a contrast product;
an actuator which is suitable for acting on the syringe in order to ensure that the contrast product flows at a pressure greater than 30 bar;
an injection outlet for injecting the contrast product towards the body of a patient, wherein the outlet is connected to the syringe;
characterised in that it further comprises:
an inflation outlet for a balloon;
a distributor which is connected at an outlet of the syringe and which is suitable for selectively connecting the same syringe to the injection outlet or to the inflation outlet;
means for controlling the distributor between a first state, which connects the syringe to the injection outlet but not to the inflation outlet, and a second state which connects the syringe to the inflation outlet;
a storage reservoir for an auxiliary fluid and means for circulating the auxiliary fluid; and
a switching valve which is interposed between the distributor and the injection outlet, wherein the switching valve is connected to the means for circulating the auxiliary fluid, and wherein the switching valve can be switched between a first state in which the means for circulating the auxiliary fluid are connected to the injection outlet and a second state in which the means for circulating the auxiliary fluid are connected to the distributor.

8. Device according to claim 7, wherein the switching valve comprises a moveable sliding valve which is held in a rest position, which defines the first state of the switching valve, under the action of a spring when there is no pressurised contrast product coming from the distributor, and wherein the sliding valve is moveable, under the action of the pressurised contrast product coming from the distributor, towards a position of passage which defines the second state of the switching valve.

9. Device according to claim 8, wherein it comprises a pressure sensor which is connected to the injection outlet via the switching valve.

10. Device according to claim 7, wherein it comprises a pressure sensor which is connected to the injection outlet via the switching valve.

11. Device according to claim 10, wherein the pressure sensor is connected to the switching valve in such a manner that the pressure sensor is connected to the injection outlet when the switching valve is in the first state thereof.

12. Medical device for distributing fluid, comprising:
a syringe for distributing a contrast product;
an actuator which is suitable for acting on the syringe in order to ensure that the contrast product flows at a pressure greater than 30 bar;
an injection outlet for injecting the contrast product towards the body of a patient, wherein the outlet is connected to the syringe;
characterised in that it further comprises:
an inflation outlet for a balloon;
a distributor which is connected at an outlet of the syringe and which is suitable for selectively connecting the same syringe to the injection outlet or to the inflation outlet;
means for controlling the distributor between a first state, which connects the syringe to the injection outlet but not to the inflation outlet, and a second state which connects the syringe to the inflation outlet;
a storage reservoir for an auxiliary fluid and means for circulating the auxiliary fluid; and
a mixer which is interposed between the distributor and the inflation outlet, and wherein the mixer is further connected to the means for circulating the auxiliary fluid in order to ensure that the contrast product and the auxiliary fluid are mixed.

13. Device according to claim 12 wherein the pressure sensor is connected to the switching valve in such a manner that the pressure sensor is connected to the injection outlet when the switching valve is in the first state thereof and the device further comprises a selector which is connected at the outlet of the means for circulating the auxiliary fluid and at the inlet of the mixer and the switching valve, and wherein the selector can be switched between a first state in which the means for circulating the auxiliary fluid are connected to the switching valve and a second state in which the means for circulating the auxiliary fluid are connected to the mixer.

14. Medical device for distributing fluid, comprising:
- a syringe for distributing a contrast product;
- an actuator which is suitable for acting on the syringe in order to ensure that the contrast product flows at a pressure greater than 30 bar;
- an injection outlet for injecting the contrast product towards the body of a patient, wherein the outlet is connected to the syringe, characterised in that it further comprises:
- an inflation outlet for a balloon;
- a distributor which is connected at an outlet of the syringe and which is suitable for selectively connecting the same syringe to the injection outlet or to the inflation outlet;
- means for controlling the distributor between a first state, which connects the syringe to the injection outlet but not to the inflation outlet, and a second state which connects the syringe to the inflation outlet, and
- means for following up and adjusting the pressure of the contrast product at the outlet of the syringe.

* * * * *